US008145437B2

(12) United States Patent
Biro

(10) Patent No.: US 8,145,437 B2
(45) Date of Patent: Mar. 27, 2012

(54) SYSTEM AND METHOD TO OBTAIN OLIGO-PEPTIDES WITH SPECIFIC HIGH AFFINITY TO QUERY PROTEINS

(76) Inventor: Jan Biro, San Francisco, CA (US)

( * ) Notice: Subject to any disclaimer, the term of this patent is extended or adjusted under 35 U.S.C. 154(b) by 1176 days.

(21) Appl. No.: 11/473,745

(22) Filed: Jun. 23, 2006

(65) Prior Publication Data

US 2007/0015189 A1 Jan. 18, 2007

Related U.S. Application Data

(60) Provisional application No. 60/694,055, filed on Jun. 24, 2005.

(51) Int. Cl.
*C40B 30/02* (2006.01)
*G06F 19/00* (2006.01)

(52) U.S. Cl. ......... 702/20; 435/6.12; 435/6.13; 435/7.1; 435/69.1

(58) Field of Classification Search ........................ None
See application file for complete search history.

(56) References Cited

OTHER PUBLICATIONS

Jan C. Biro, A novel intra-molecular protein-protein interaction code based on partial complementary coding of co-locating amino acids, Medical Hypotheses (2006), vol. 66, pp. 137-142, available online on Sep. 15, 2005.*
Root-Bernstein. J. Theor. Biol., 1998, 190, 107-119.*
Heal et al. ChemBioChem 2002, 3, 136-151.*
Biro J. Biochemical and Biophysical Research Communications 306 (2003) 408-415.*
Biro, JC: Principia Biroinformatica—Creative Ideas in Molecular Biology—Nov. 2009, 2nd Edition, 620 pages on CD, Ed.: Homulus Fnd,. Los Angeles, USA.
Biro, JC: Principia Biroinformatica—The Proteomic Code—Dec. 2009, 1st Edition, 184 pages, Ed.: Homulus Fnd., Los Angeles, USA.

* cited by examiner

*Primary Examiner* — Michael Borin

(57) ABSTRACT

This application is based on the concept of the Proteomic Code, PC (discovered and described by Biro, 1981-2011, for review see ref 6) and making use of the biological observation, that co-locating amino acids [in interacting proteins] are coded by partially complementary codons. A method is provided to design and produce a special and distinct set of affinity oligopeptides (AffiSeq) using the PC principle. These designed and artificially produced affinity peptides will be used in any biotechnological or pharmacological applications which benefit of the specific and high affinity protein-protein interactions.

2 Claims, 11 Drawing Sheets

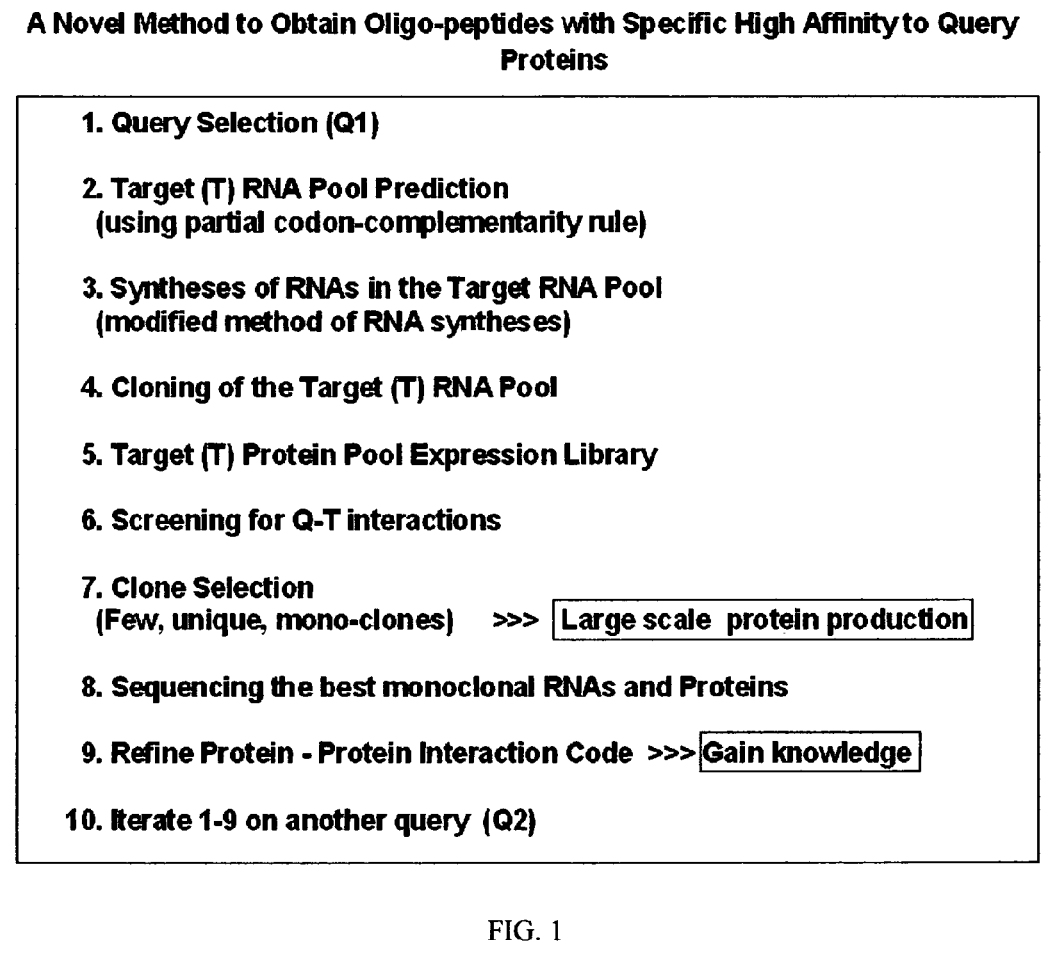

A Novel Method to Obtain Oligo-peptides with Specific High Affinity to Query Proteins

1. Query Selection (Q1)
2. Target (T) RNA Pool Prediction
   (using partial codon-complementarity rule)
3. Syntheses of RNAs in the Target RNA Pool
   (modified method of RNA syntheses)
4. Cloning of the Target (T) RNA Pool
5. Target (T) Protein Pool Expression Library
6. Screening for Q-T interactions
7. Clone Selection
   (Few, unique, mono-clones) >>> Large scale protein production
8. Sequencing the best monoclonal RNAs and Proteins
9. Refine Protein - Protein Interaction Code >>> Gain knowledge
10. Iterate 1-9 on another query (Q2)

FIG. 1

```
1. Query Selection (Q)

A.
>V00565 | HSINSU Human Preproinsulin Peptide, 114
MALWMRLLPLLALLALWGPDPAAAFVNQHLCGSHLVEALYLVCGERGF
FYTPKTRREAEDLQVGQVELGGGPGAGSLQPLALEGSLQKRGIVEQCCTS
ICSLYQLENYCN

>V00565 | HSINSU Human Preproinsulin CDS, 333
atggccctgt ggatgcgcct cctgcccctg ctggcgctgc tggccctctg
gggacctgac ccagccgcag cctttgtgaa ccaacacctg tgcggctcac
acctggtgga agctctctac ctagtgtgcg gggaacgagg cttcttctac
acacccaaga cccgccggga ggcagaggac ctgcaggtgg ggcaggtgga
gctgggcggg ggccctggtg caggcagcct gcagcccttg gccctggagg
ggtccctgca gaagcgtggc attgtggaac aatgctgtac cagcatctgc
tccctctacc agctggagaa ctactgcaac tag

B.
>HS Insulin Peptide A
ggc.att.gtg.gaa.caa.tgc.tgt.acc.agc.atc.tgc.tcc.ctc.tac.cag.ctg.gag.
 G   I   V   E   Q   C   C   T   S   I   C   S   L   Y   Q   L   E
aac.tac.tgc.aac.tag
 N   Y   C   N   *

C.
>HS Insulin Peptide A 1-10
5'                                     3'
ggc.att.gtg.gaa.caa.tgc.tgt.acc.agc.atc.
 G   I   V   E   Q   C   C   T   S   I
```

---

```
2. Target (T) RNA Pool Prediction
(using partial codon complementary rule)

A.
                          5'                                      3'
Direct:                   ggc.att.gtg.gaa.caa.tgc.tgt.acc.agc.atc
Complement:               cng.tna.cnc.cnt.gnt.ang.ana.tng.tng.tng
                          3'                                      5'

B.
                          5'                                      3'
Reverse & Complement:     gnu.gnu.gnu.ana.gna.ung.unc.cnc.anu.gnc


n is a, c, g, or u(t)
```

FIG. 2

Syntheses of RNAs in Target RNA Pool
(modified method of RNA syntheses)

| 1$^{st}$ Step | 2$^{nd}$ Step | 5$^{th}$ Step | 6$^{th}$ Step | 7$^{th}$ Step |
|---|---|---|---|---|
| 5' | GA | GAU.GA | GAU.GAU | GAU.GAU.G |
| G | GU | GUU.GA | GUU.GAU | GUU.GAU.G |
| | GG | GGU.GA | GGU.GAU | GGU.GAU.G |
| | GC | GCU.GA | GCU.GAU | GCU.GAU.G |
| | | GAU.GU | GAU.GUU | GAU.GUU.G |
| | 3$^{rd}$ Step | GUU.GU | GUU.GUU | GUU.GUU.G |
| | GAU | GGU.GU | GGU.GUU | GGU.GUU.G |
| | GUU | GCU.GU | GCU.GUU | GCU.GUU.G |
| | GGU | GAU.GG | GAU.GGU | GAU.GGU.G |
| | GCU | GUU.GG | GUU.GGU | GUU.GGU.G |
| | | GGU.GG | GGU.GGU | GGU.GGU.G |
| | 4$^{th}$ Step | GCU.GG | GCU.GGU | GCU.GGU.G |
| | GAU.G | GAU.GC | GAU.GCU | GAU.GCU.G |
| | GUU.G | GUU.GC | GUU.GCU | GUU.GCU.G |
| | GGU.G | GGU.GC | GGU.GCU | GGU.GCU.G |
| | GCU.G | GCU.GC | GCU.GCU | GCU.GCU.G |

Bold & underlined codons indicate the addition of nucleotide mixture

FIG. 3

Target Oligo- Nucleotide Templates (TONT)

```
>DNA Artificial Target Template to ESRLERLEQLFLLIF (GAL4
09-23 AA)-ssDNA-sense
5'-gga.tcc--atg--[ana.ant.cng.tng.ana.tng.cng.tnc.cng.tnt.
----BamHI---Met--[-------VARIABLE SEQUENCE, TONT-V ~30-45
NA

tnc.tng.cnt.tna.tnc.]--att--cgg.ccg.c- 3'
-------------------]--STOP--NotI-----


>DNA Artificial Target Template to QLFLLIFPREDLDMI (GAL4
17-31 AA)-ssDNA-sense
5'-gga.tcc--atg--[ant.cnt.gnc.ang.gnc.tnc.tng.ang.ana.ant.
----BamHI---Met--[-------VARIABLE SEQUENCE, TONT-V ~30-45
NA

cng.tng.ana.tng.cng]--att--cgg.ccg.c- 3'
-------------------]--STOP--NotI-----
```

FIG. 5

Expression of Target Oligo- Nucleotide Templates (TONT)

>RNA Artificial Target Oligo Template to ESRLERLEQLFLLIF (GAL4 09-23AA)-mRNA

5'-aug--[ana.anu.cng.ung.ana.ung.cng.unc.cng.unu.unc.ung.cnu.una.unc]--auu--3'

PROTEIN A ($4^{15}$ SEQUENCES)

M-1-2-3-4-5-6-7-8-9-10-11-12-13-14-15-END

H2N--------------------------------COOH

>RNA Artificial Target Oligo Template to QLFFLLIFPREDLDMI (GAL4 17-31AA)-mRNA

5'--aug-[anu.cnu.gnc.ang.gnc.unc.ung.ang.ana.anu.cng.ung.ana.ung.cng]--auu--3'

PROTEIN B ($4^{15}$ SEQUENCES)

M-1-2-3-4-5-6-7-8-9-10-11-12-13-14-15-END

H2N--------------------------------COOH

FIG. 6

Proinsulin (PINS) Query Oligo- Peptides (QOP)

>PINS_QP: X70508_HS mRNA for pre-proinsulin,
MALWMRLLPLLALLALWGPDPAAAFVNQHLCGSHLVEALYLVCGERGFFY
TPKTRREAEDLQVGQVELGGGPGAGSLQPLALEGSLQKRGIVEQCCTSIC
SLYQLENYCN >PINS_QOP3
VNQHLCGSHLVEAL
>PINS_QOP4
YLVCGERGFFYTPK
>PINS_QOP5
EAEDLQVGQVELGG
>PINS_QOP6
GPGAGSLQPLALEG
>PINS_QOP7
KRGIVEQCCTSI

>MYC_COP: TAG,CONTROL
EQKLISEEDL

FIG 7.

Target Oligo- Nucleotide Template (TONT) Designs from Proinsulin (PINS) Sequences

```
5'--RE1--//---------------Cys.TONT, (30-45 na.) ------------//--------
MYC_CON----------//--RE2-3'


>PINS_TONT3+MYC
5--TGC.GNG.ANC.TNC.CNC.CNG.GNG.TNA.GNC.GNA.CNG.GNG.TNG.GNT.CNC.-
GAG.CAG.AAG.CTC.ATC.TCC.GAG.GAG.GAC.CTC.

>PINS_TONT4+MYC
5'--TGC.CNT.GNG.TNT.GNA.GNA.GNA.GNC.TNG.TNC.CNC.GNA.CNC.TNG.GNA.-
GAG.CAG.AAG.CTC.ATC.TCC.GAG.GAG.GAC.CTC.

>PINS_TONT5+MYC
5'--TGC.CNC.GNC.CNG.CNC.CNC.CNG.CNC.CNC.CNG.CNG.GNC.CNC.TNC.CNC.-
GAG.CAG.AAG.CTC.ATC.TCC.GAG.GAG.GAC.CTC.

>PINS_TONT6+MYC
5'--TGC.CNC.CNC.CNG.GNC.CNA.GNG.CNG.CNG.GNT.GNC.TNC.ANC.ANG.GNC.-
GAG.CAG.AAG.CTC.ATC.TCC.GAG.GAG.GAC.CTC.

>PINS_TONT7+MYC
5'--TGC.GNT.GNT.GNT.ANA.GNA.TNG.TNC.CNC.ANT.GNC.ANG.CNT.-
GAG.CAG.AAG.CTC.ATC.TCC.GAG.GAG.GAC.CTC.


>MYC_CON: tag, Control
GAG.CAG.AAG.CTC.ATC.TCC.GAG.GAG.GAC.CTC
```

FIG 8.

Target Oligo- Peptides (TOP) Designed to Bind to Proinsulin (PIN) Query Oligo- Peptides (QOP)

>PINS_TOP3+MYC
C-GG-SSLLVSVAQASGL–*EQKLISEEDL*

>PINS_TOP4+MYC
C-GG-EFAEGAWSLARLV-EQKLISEEDL

>PINS_TOP5+MYC
C-GG-APPLPHPRLGPSL—EQKLISEEDL

>PINS_TOP6+MYC
C-GG-PQGPAPLGACTRV-EQKLISEEDL

>PINS_TOP7+MYC
C-GG-DADTEWCRNAMP–EQKLISEEDL

>MYC-COP
C-GG-EQKLISEEDL

FIG 9

Binding of Proinsulin (PINS) Query Oligo- Peptides (QOP) to Designed Target Oligo- Peptides (TOP)

| | QOP3 | QOP4 | QOP5 | QOP6 | QOP7 | MYC_MAB | BSA |
|---|---|---|---|---|---|---|---|
| TOP3+MYC | 1.7μM | N/A | N/A | N/A | N/A | 1nM | N/A |
| TOP4+MYC | N/A | 90μM | N/A | N/A | N/A | 1nM | N/A |
| TOP5+MYC | N/A | N/A | 150μM | N/A | N/A | 5nM | N/A |
| TOP6+MYC | N/A | N/A | N/A | 0.1μM | N/A | 1nM | N/A |
| TOP7+MYC | N/A | N/A | N/A | N/A | 72μM | 5nM | N/A |
| | | | | | | | |
| MYC-COP | N/A | N/A | N/A | N/A | N/A | 3nM | N/A |
| BSA | N/A | N/A | N/A | N/A | N/A | N/A | N/A |

FIG 11.

```
                         SEQUENCE LISTING


<160> NUMBER OF SEQ ID NOS: 92

<210> SEQ ID NO 1
<211> LENGTH: 114
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
  1               5                  10                  15

Trp Gly Pro Asp Pro Ala Ala Ala Phe Val Asn Gln His Leu Cys Gly
             20                  25                  30

Ser His Leu Val Glu Ala Leu Tyr Leu Val Cys Gly Glu Phe Thr Arg
         35                  40                  45

Gly Phe Phe Tyr Thr Pro Lys Thr Arg Arg Glu Ala Asp Glu Asp Leu
     50                  55                  60

Gln Val Gly Gln Val Glu Leu Gly Gly Gly Pro Gly Ala Gly Ser Leu
 65                  70                  75                  80

Gln Pro Leu Ala Leu Glu Gly Ser Leu Gln Lys Arg Gly Ile Val Gln
                 85                  90                  95

Cys Cys Thr Ser Ile Cys Ser Leu Tyr Gln Phe Thr Leu Glu Asn Tyr
            100                 105                 110

Cys Asn


<210> SEQ ID NO 2
<211> LENGTH: 333
<212> TYPE: DNA
<213> ORGANISM: Homo sapiens

<400> SEQUENCE: 2

atggccctgt ggatgcgcct cctgcccctg ctggcgctgc tggccctctg gggacctgac      60

ccagccgcag cctttgtgaa ccaacacctg tgcggctcac acctggtgga agctctctac     120
```

ctagtgtgcg gggaacgagg cttcttctac acacccaaga cccgccggga ggcagaggac 180
ctgcaggtgg ggcaggtgga gctgggcggg ggccctggtg caggcagcct gcagcccttg 240
gccctggagg ggtccctgca gaagcgtggc attgtggaac aatgctgtac cagcatctgc 300
tccctctacc agctggagaa ctactgcaac tag 333

<210> SEQ ID NO 3
<211> LENGTH: 66
<212> TYPE: DNA
<213> ORGANISM: Homo sapiens

<400> SEQUENCE: 3
ggcattgtgg aacaatgctg taccagcatc tgctccctct accagctgga gaactactgc 60
aactag 66

<210> SEQ ID NO 4
<211> LENGTH: 21
<212> TYPE: PRT
<213> ORGANISM: Homo sapiens

<400> SEQUENCE: 4

Gly Ile Val Glu Gln Cys Cys Thr Ser Ile Cys Ser Leu Tyr Gln Leu
1 5 10 15

Glu Asn Tyr Cys Asn
20

<210> SEQ ID NO 5
<211> LENGTH: 30
<212> TYPE: DNA
<213> ORGANISM: Homo sapiens

<400> SEQUENCE: 5
ggcattgtgg aacaatgctg taccagcatc 30

<210> SEQ ID NO 6
<211> LENGTH: 10
<212> TYPE: PRT
<213> ORGANISM: Homo sapiens

<400> SEQUENCE: 6

Gly Ile Val Glu Gln Cys Cys Thr Ser Ile
1 5 10

<210> SEQ ID NO 7
<211> LENGTH: 30
<212> TYPE: DNA
<213> ORGANISM: Artificial
<220> FEATURE:
<223> OTHER INFORMATION: Target RNA Pool Prediction
(using partial codon complementary rule)

<400> SEQUENCE: 7
ggcattgtgg aacaatgctg taccagcatc 30

<210> SEQ ID NO 8
<211> LENGTH: 30
<212> TYPE: DNA
<213> ORGANISM: Artificial Sequence
<220> FEATURE:
<223> OTHER INFORMATION: Complement to SEQ ID NO: 7, for Target RNA Pool
Prediction, using partial codon complementary rule. Designed using
Proteomic Code (J.C.Biro)
<220> FEATURE:
<221> NAME/KEY: misc_feature
<222> LOCATION: (1)..(30)

<223> OTHER INFORMATION: n is a, c, g, or t

<400> SEQUENCE: 8
cngtnacncc ntgntangan atngtngtng 30

<210> SEQ ID NO 9
<211> LENGTH: 30
<212> TYPE: RNA
<213> ORGANISM: Artificial
<220> FEATURE:
<223> OTHER INFORMATION: Reverse and Complement to SEQ ID NO: 7, Target RNA Pool Prediction, using partial codon complementary data. Designed using Proteomic Code (J.C.Biro)
<220> FEATURE:
<221> NAME/KEY: misc_feature
<222> LOCATION: (2)..(2)
<223> OTHER INFORMATION: n is a, c, g or u
<220> FEATURE:
<221> NAME/KEY: misc_feature
<222> LOCATION: (5)..(5)
<223> OTHER INFORMATION: n is a, c, g or u
<220> FEATURE:
<221> NAME/KEY: misc_feature
<222> LOCATION: (8)..(8)
<223> OTHER INFORMATION: n is a, c, g or u
<220> FEATURE:
<221> NAME/KEY: misc_feature
<222> LOCATION: (11)..(11)
<223> OTHER INFORMATION: n is a, c, g or u
<220> FEATURE:
<221> NAME/KEY: misc_feature
<222> LOCATION: (14)..(14)
<223> OTHER INFORMATION: n is a, c, g or u
<220> FEATURE:
<221> NAME/KEY: misc_feature
<222> LOCATION: (17)..(17)
<223> OTHER INFORMATION: n is a, c, g or u
<220> FEATURE:
<221> NAME/KEY: misc_feature
<222> LOCATION: (20)..(20)
<223> OTHER INFORMATION: n is a, c, g or u
<220> FEATURE:
<221> NAME/KEY: misc_feature
<222> LOCATION: (23)..(23)
<223> OTHER INFORMATION: n is a, c, g or u
<220> FEATURE:
<221> NAME/KEY: misc_feature
<222> LOCATION: (26)..(26)
<223> OTHER INFORMATION: n is a, c, g, or u
<220> FEATURE:
<221> NAME/KEY: misc_feature
<222> LOCATION: (29)..(29)
<223> OTHER INFORMATION: n is a, c, g, or u

<400> SEQUENCE: 9
gnugnugnua nagnaungun ccncanugnc 30

<210> SEQ ID NO 10
<211> LENGTH: 1
<212> TYPE: RNA
<213> ORGANISM: Artificial
<220> FEATURE:
<223> OTHER INFORMATION: Synthesis of RNA5 in Target RNA Pool, modified method of RNA syntheses. Designed using Proteomic Code (J.C.Biro)

<400> SEQUENCE: 10 g 1

<210> SEQ ID NO 11
<211> LENGTH: 2
<212> TYPE: RNA
<213> ORGANISM: Artificial
<220> FEATURE:
<223> OTHER INFORMATION: Synthesis of RNAS in Target RNA Pool, modified -continued

```
      method of RNA syntheses. Designed using Proteomic Code (J.C.Biro)

<400> SEQUENCE: 11

ga                                                                       2


<210> SEQ ID NO 12
<211> LENGTH: 2
<212> TYPE: RNA
<213> ORGANISM: Artificial
<220> FEATURE:
<223> OTHER INFORMATION: Synthesis of RNAS in Target RNA Pool, modified
      method of RNA syntheses. Designed using Proteomic Code (J.C.Biro)

<400> SEQUENCE: 12

gu                                                                       2


<210> SEQ ID NO 13
<211> LENGTH: 2
<212> TYPE: RNA
<213> ORGANISM: Artificial
<220> FEATURE:
<223> OTHER INFORMATION: Synthesis of RNAS in Target RNA Pool, modified
      method of RNA syntheses. Designed using Proteomic Code (J.C.Biro)

<400> SEQUENCE: 13

gg                                                                       2


<210> SEQ ID NO 14
<211> LENGTH: 2
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 14

gc                                                                       2


<210> SEQ ID NO 15
<211> LENGTH: 3
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 15

gau                                                                      3


<210> SEQ ID NO 16
<211> LENGTH: 3
<212> TYPE: RNA
<213> ORGANISM: Artificial
<220> FEATURE:
<223> OTHER INFORMATION: Synthesis of RNAS in Target RNA Pool, modified
      method of RNA syntheses. Designed using Proteomic Code (J.C.Biro)

<400> SEQUENCE: 16

guu                                                                      3


<210> SEQ ID NO 17
<211> LENGTH: 3
<212> TYPE: RNA
<213> ORGANISM: Artificial
<220> FEATURE:
<223> OTHER INFORMATION: Synthesis of RNAS in Target RNA Pool, modified
      method of RNA syntheses. Designed using Proteomic Code (J.C.Biro)
```

<400> SEQUENCE: 17 ggu 3

<210> SEQ ID NO 18
<211> LENGTH: 3
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 18 gcu 3

<210> SEQ ID NO 19
<211> LENGTH: 4
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 19 gaug 4

<210> SEQ ID NO 20
<211> LENGTH: 4
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 20 guug 4

<210> SEQ ID NO 21
<211> LENGTH: 4
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 21 ggug 4

<210> SEQ ID NO 22
<211> LENGTH: 4
<212> TYPE: RNA
<213> ORGANISM: Artificial
<220> FEATURE:
<223> OTHER INFORMATION: Synthesis of RNA5 in Target RNA Pool, modified method of RNA syntheses. Designed using Proteomic Code (J.C.Biro)

<400> SEQUENCE: 22 gcug 4

<210> SEQ ID NO 23
<211> LENGTH: 5
<212> TYPE: RNA
<213> ORGANISM: Artificial
<220> FEATURE:
<223> OTHER INFORMATION: Synthesis of RNAS in Target RNA Pool, modified method of RNA. Designed using Proteomic Code (J.C.Biro)

<400> SEQUENCE: 23

-continued gauga 5

<210> SEQ ID NO 24
<211> LENGTH: 5
<212> TYPE: RNA
<213> ORGANISM: Artificial
<220> FEATURE:
<223> OTHER INFORMATION: synthesis of RNA5 in Target RNA Pool, modified method of RNA syntheses. Designed using Proteomic Code (J.C.Biro)

<400> SEQUENCE: 24 guuga 5

<210> SEQ ID NO 25
<211> LENGTH: 5
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 25 gguga 5

<210> SEQ ID NO 26
<211> LENGTH: 5
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 26 gcuga 5

<210> SEQ ID NO 27
<211> LENGTH: 5
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 27 gaugu 5

<210> SEQ ID NO 28
<211> LENGTH: 5
<212> TYPE: RNA
<213> ORGANISM: Artificial
<220> FEATURE:
<223> OTHER INFORMATION: synthesis of RNAS in Target RNA Pool, modified method of RNA Syntheses. Designed using Proteomic Code (J.C.Biro)

<400> SEQUENCE: 28 guugu 5

<210> SEQ ID NO 29
<211> LENGTH: 5
<212> TYPE: RNA
<213> ORGANISM: Artificial
<220> FEATURE:
<223> OTHER INFORMATION: synthesis of RNA5 in Target RNA Pool, modified method of RNA syntheses. Designed using Proteomic Code (J.C.Biro)

<400> SEQUENCE: 29 ggugu 5

```
<210> SEQ ID NO 30
<211> LENGTH: 5
<212> TYPE: RNA
<213> ORGANISM: Artificial
<220> FEATURE:
<223> OTHER INFORMATION: synthesis of RNA5 in Target RNA Pool, modified
      method of RNA syntheses. Designed using Proteomic Code (J.C.Biro)

<400> SEQUENCE: 30

gcugu                                                                  5


<210> SEQ ID NO 31
<211> LENGTH: 5
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 31

gaugg                                                                  5


<210> SEQ ID NO 32
<211> LENGTH: 5
<212> TYPE: RNA
<213> ORGANISM: Artificial
<220> FEATURE:
<223> OTHER INFORMATION: synthesis of RNAS in Target RNA Pool, modified
      method of RNA-syntheses. Designed using Proteomic Code (J.C.Biro)

<400> SEQUENCE: 32

guugg                                                                  5


<210> SEQ ID NO 33
<211> LENGTH: 5
<212> TYPE: RNA
<213> ORGANISM: Artificial
<220> FEATURE:
<223> OTHER INFORMATION: Synthesis of RNAS in Target RNA Pool, modified
      method of RNA Syntheses. Designed using Proteomic Code (J.C.Biro)

<400> SEQUENCE: 33

ggugg                                                                  5


<210> SEQ ID NO 34
<211> LENGTH: 5
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 34

gcugg                                                                  5


<210> SEQ ID NO 35
<211> LENGTH: 5
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 35

gaugc                                                                  5


<210> SEQ ID NO 36
```

```
<211> LENGTH: 5
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 36

guugc                                                                 5


<210> SEQ ID NO 37
<211> LENGTH: 5
<212> TYPE: RNA
<213> ORGANISM: Artificial
<220> FEATURE:
<223> OTHER INFORMATION: Synthesis of RNAS in Target RNA Pool, modified
      method of RNA syntheses. Designed using Proteomic Code (J.C.Biro)

<400> SEQUENCE: 37

ggugc                                                                 5


<210> SEQ ID NO 38
<211> LENGTH: 5
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 38

gcugc                                                                 5


<210> SEQ ID NO 39
<211> LENGTH: 6
<212> TYPE: RNA
<213> ORGANISM: Artificial
<220> FEATURE:
<223> OTHER INFORMATION: synthesis of RNAS in Target RNA Pool, modified
      method of RNA syntheses. Designed using Proteomic Code (J.C.Biro)

<400> SEQUENCE: 39

gaugau                                                                6


<210> SEQ ID NO 40
<211> LENGTH: 6
<212> TYPE: RNA
<213> ORGANISM: Artificial
<220> FEATURE:
<223> OTHER INFORMATION: synthesis of RNAS in Target RNA Pool, modified
      method of RNA syntheses

<400> SEQUENCE: 40

guugau                                                                6


<210> SEQ ID NO 41
<211> LENGTH: 6
<212> TYPE: RNA
<213> ORGANISM: Artificial
<220> FEATURE:
<223> OTHER INFORMATION: synthesis of RNAs in Target RNA Pool, modified
      method of RNA syntheses. Designed using Proteomic Code (J.C.Biro)

<400> SEQUENCE: 41

ggugau                                                                6


<210> SEQ ID NO 42
<211> LENGTH: 6
<212> TYPE: RNA
```

<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 42 gcugau 6

<210> SEQ ID NO 43
<211> LENGTH: 6
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 43 gauguu 6

<210> SEQ ID NO 44
<211> LENGTH: 6
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 44 guuguu 6

<210> SEQ ID NO 45
<211> LENGTH: 6
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 45 gguguu 6

<210> SEQ ID NO 46
<211> LENGTH: 6
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 46 gcuguu 6

<210> SEQ ID NO 47
<211> LENGTH: 6
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 47 gauggu 6

<210> SEQ ID NO 48
<211> LENGTH: 6
<212> TYPE: RNA
<213> ORGANISM: Artificial
<220> FEATURE:

<223> OTHER INFORMATION: synthesis of RNAS in Target RNA Pool, modified method of RNA syntheses. Designed using Proteomic Code (J.C.Biro)

<400> SEQUENCE: 48 guuggu 6

<210> SEQ ID NO 49
<211> LENGTH: 6
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 49 gguggu 6

<210> SEQ ID NO 50
<211> LENGTH: 6
<212> TYPE: RNA
<213> ORGANISM: Artificial
<220> FEATURE:
<223> OTHER INFORMATION: synthesis of RNA5 in Target RNA Pool, modified method of RNA syntheses. Designed using Proteomic Code (J.C.Biro)

<400> SEQUENCE: 50 gcuggu 6

<210> SEQ ID NO 51
<211> LENGTH: 6
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 51 gaugcu 6

<210> SEQ ID NO 52
<211> LENGTH: 6
<212> TYPE: RNA
<213> ORGANISM: Artificial
<220> FEATURE:
<223> OTHER INFORMATION: Synthesis of RNAS in Target RNA Pool, modified method of RNA syntheses

<400> SEQUENCE: 52 guugcu 6

<210> SEQ ID NO 53
<211> LENGTH: 6
<212> TYPE: RNA
<213> ORGANISM: Artificial
<220> FEATURE:
<223> OTHER INFORMATION: synthesis of RNA5 in Target RNA Pool, modified method of RNA syntheses. Designed using Proteomic Code (J.C.Biro)

<400> SEQUENCE: 53 ggugcu 6

<210> SEQ ID NO 54
<211> LENGTH: 6
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 54 gcugcu 6

<210> SEQ ID NO 55
<211> LENGTH: 7
<212> TYPE: RNA
<213> ORGANISM: Artificial
<220> FEATURE:
<223> OTHER INFORMATION: synthesis of RNA5 in Target RNA Pool, modified method of RNA syntheses. Designed using Proteomic Code (J.C.Biro)

<400> SEQUENCE: 55 gaugaug 7

<210> SEQ ID NO 56
<211> LENGTH: 7
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 56 guugaug 7

<210> SEQ ID NO 57
<211> LENGTH: 7
<212> TYPE: RNA
<213> ORGANISM: Artificial
<220> FEATURE:
<223> OTHER INFORMATION: Synthesis of RNAs in Target RNA Pool, modified method of RNA syntheses. Designed using Proteomic Code (J.C.Biro)

<400> SEQUENCE: 57 ggugaug 7

<210> SEQ ID NO 58
<211> LENGTH: 7
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 58 gcugaug 7

<210> SEQ ID NO 59
<211> LENGTH: 7
<212> TYPE: RNA
<213> ORGANISM: Artificial
<220> FEATURE:
<223> OTHER INFORMATION: synthesis of RNA5 in Target RNA Pool, modified method of RNA syntheses. Designed using Proteomic Code (J.C.Biro)

<400> SEQUENCE: 59 gauguug 7

<210> SEQ ID NO 60
<211> LENGTH: 7
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 60

-continued guuguug 7

<210> SEQ ID NO 61
<211> LENGTH: 7
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 61 gguguug 7

<210> SEQ ID NO 62
<211> LENGTH: 7
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 62 gcuguug 7

<210> SEQ ID NO 63
<211> LENGTH: 7
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 63 gauggug 7

<210> SEQ ID NO 64
<211> LENGTH: 7
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 64 guuggug 7

<210> SEQ ID NO 65
<211> LENGTH: 7
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 65 gguggug 7

<210> SEQ ID NO 66
<211> LENGTH: 7
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 66 gcuggug 7

<210> SEQ ID NO 67
<211> LENGTH: 7
<212> TYPE: RNA
<213> ORGANISM: Artificial
<220> FEATURE:
<223> OTHER INFORMATION: synthesis of RNAS in Target RNA Pool, modified method of RNA syntheses. Designed using Proteomic Code (J.C.Biro)

<400> SEQUENCE: 67 gaugcug 7

<210> SEQ ID NO 68
<211> LENGTH: 7
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 68 guugcug 7

<210> SEQ ID NO 69
<211> LENGTH: 7
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 69 ggugcug 7

<210> SEQ ID NO 70
<211> LENGTH: 7
<212> TYPE: RNA
<213> ORGANISM: Artificial
<220> FEATURE:
<223> OTHER INFORMATION: Synthesis of RNAS in Target RNA Pool, modified method of RNA syntheses. Designed using Proteomic Code (J.C.Biro)

<400> SEQUENCE: 70 gcugcug 7

<210> SEQ ID NO 71
<211> LENGTH: 64
<212> TYPE: DNA
<213> ORGANISM: Artificial
<220> FEATURE:
<223> OTHER INFORMATION: Target Template to ESRLERLEQLFLLIF (GAL4 09-23 AA)-ssDNA-sense. Designed using Proteomic Code (J.C.Biro)
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g or t
<220> FEATURE:
<221> NAME/KEY: misc_feature
<222> LOCATION: (17)..(17)
<223> OTHER INFORMATION: n is a, c, g or t
<220> FEATURE:
<221> NAME/KEY: misc_feature
<222> LOCATION: (20)..(20)
<223> OTHER INFORMATION: n is a, c, g or t
<220> FEATURE:
<221> NAME/KEY: misc_feature
<222> LOCATION: (23)..(23)

<223> OTHER INFORMATION: n is a, c, g or t
<220> FEATURE:
<221> NAME/KEY: misc_feature
<222> LOCATION: (26)..(26)
<223> OTHER INFORMATION: n is a, c, g or t
<220> FEATURE:
<221> NAME/KEY: misc_feature
<222> LOCATION: (29)..(29)
<223> OTHER INFORMATION: n is a, c, g or t
<220> FEATURE:
<221> NAME/KEY: misc_feature
<222> LOCATION: (32)..(32)
<223> OTHER INFORMATION: n is a, c, g or t
<220> FEATURE:
<221> NAME/KEY: misc_feature
<222> LOCATION: (35)..(35)
<223> OTHER INFORMATION: n is a, c, g or t
<220> FEATURE:
<221> NAME/KEY: misc_feature
<222> LOCATION: (38)..(38)
<223> OTHER INFORMATION: n is a, c, g or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 71
ggatccatga naantcngtn ganatngcng tnccngtntt nctngcnttn atncattcgg 60
ccgc 64

<210> SEQ ID NO 72
<211> LENGTH: 64
<212> TYPE: DNA
<213> ORGANISM: Artificial
<220> FEATURE:
<223> OTHER INFORMATION: Target Template to QLFLLIFPREDLDMI (GAL4 17-31AA)-s5DNA-sense. Designed using Proteomic Code (J.C.Biro)
<220> FEATURE:
<221> NAME/KEY: misc_feature
<222> LOCATION: (11) .. (11)
<223> OTHER INFORMATION: n is a, c, g or t
<220> FEATURE:
<221> NAME/KEY: misc_feature
<222> LOCATION: (14)..(14)
<223> OTHER INFORMATION: n is a, c, g or t
<220> FEATURE:
<221> NAME/KEY: misc_feature
<222> LOCATION: (17)..(17)
<223> OTHER INFORMATION: n is a, c, g or t
<220> FEATURE:
<221> NAME/KEY: misc_feature
<222> LOCATION: (20)..(20)
<223> OTHER INFORMATION: n is a, c, g or t
<220> FEATURE:
<221> NAME/KEY: misc_feature
<222> LOCATION: (23)..(23)
<223> OTHER INFORMATION: n is a, c, g or t
<220> FEATURE:
<221> NAME/KEY: misc_feature
<222> LOCATION: (26)..(26)
<223> OTHER INFORMATION: n is a, c, g or t
<220> FEATURE:
<221> NAME/KEY: misc_feature
<222> LOCATION: (29)..(29)
<223> OTHER INFORMATION: n is a, c, g or t
<220> FEATURE:
<221> NAME/KEY: misc_feature
<222> LOCATION: (32)..(32)
<223> OTHER INFORMATION: n is a, c, g or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 72
ggatccatga ntcntgncan ggnctnctng anganaantc ngtnganatn gcngattcgg 60
ccgc 64

<210> SEQ ID NO 73
<211> LENGTH: 51
<212> TYPE: RNA
<213> ORGANISM: Artificial
<220> FEATURE:
<223> OTHER INFORMATION: Target Oligo Template to ESRLERLEQLFLLIF (GAL4 09-23AA)-mRNA. Designed using Proteomic Code (J.C.Biro)
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u
<220> FEATURE:
<221> NAME/KEY: misc_feature
<222> LOCATION: (17)..(17)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:

<221> NAME/KEY: misc_feature
<222> LOCATION: (26)..(26)
<223> OTHER INFORMATION: n is a, c, g, or u
<220> FEATURE:
<221> NAME/KEY: misc_feature
<222> LOCATION: (29)..(29)
<223> OTHER INFORMATION: n is a, c, g, or u
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (35)..(35)
<223> OTHER INFORMATION: n is a, c, g, or u
<220> FEATURE:
<221> NAME/KEY: misc_feature
<222> LOCATION: (38)..(38)
<223> OTHER INFORMATION: n is a, c, g, or u
<220> FEATURE:
<221> NAME/KEY: misc_feature
<222> LOCATION: (41)..(41)
<223> OTHER INFORMATION: n is a, c, g, or u
<220> FEATURE:
<221> NAME/KEY: misc_feature
<222> LOCATION: (44)..(44)
<223> OTHER INFORMATION: n is a, c, g, or u
<220> FEATURE:
<221> NAME/KEY: misc_feature
<222> LOCATION: (47)..(47)
<223> OTHER INFORMATION: n is a, c, g, or u

<400> SEQUENCE: 73
auganaanuc ngunganaun gcngunccng unuuncungc nuunauncau u 51

<210> SEQ ID NO 74
<211> LENGTH: 51
<212> TYPE: RNA
<213> ORGANISM: Artificial
<220> FEATURE:
<223> OTHER INFORMATION: Target Oligo Template to QLFFLLIFPREDLDMI (GAL4 17-31AA)-mRNA. Designed using Proteomic Code (J.C.Biro)
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u
<220> FEATURE:
<221> NAME/KEY: misc_feature
<222> LOCATION: (17)..(17)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (26)..(26)
<223> OTHER INFORMATION: n is a, c, g, or u
<220> FEATURE:
<221> NAME/KEY: misc_feature
<222> LOCATION: (29)..(29)
<223> OTHER INFORMATION: n is a, c, g, or u -continued
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (35)..(35)
<223> OTHER INFORMATION: n is a, c, g or u
<220> FEATURE:
<221> NAME/KEY: misc_feature
<222> LOCATION: (38)..(38)
<223> OTHER INFORMATION: n is a, c, g or u
<220> FEATURE:
<221> NAME/KEY: misc_feature
<222> LOCATION: (41)..(41)
<223> OTHER INFORMATION: n is a, c, g or u
<220> FEATURE:
<221> NAME/KEY: misc_feature
<222> LOCATION: (44)..(44)
<223> OTHER INFORMATION: n is a, c, g or u
<220> FEATURE:
<221> NAME/KEY: misc_feature
<222> LOCATION: (47)..(47)
<223> OTHER INFORMATION: n is a, c, g or u

<400> SEQUENCE: 74
auganucnug ncanggncun cungangana anucngunga naungcngau u 51

<210> SEQ ID NO 75
<211> LENGTH: 14
<212> TYPE: PRT
<213> ORGANISM: Homo Sapiens

<400> SEQUENCE: 75

Val Asn Gln His Leu Cys Gly Ser His Leu Val Glu Ala Leu
1 5 10

<210> SEQ ID NO 76
<211> LENGTH: 14
<212> TYPE: PRT
<213> ORGANISM: Homo Sapiens

<400> SEQUENCE: 76

Tyr Leu Val Cys Gly Glu Arg Gly Phe Phe Tyr Thr Pro Lys
1 5 10

<210> SEQ ID NO 77
<211> LENGTH: 14
<212> TYPE: PRT
<213> ORGANISM: Homo Sapiens

<400> SEQUENCE: 77

Glu Ala Glu Asp Leu Gln Val Gly Gln Val Glu Leu Gly Gly
1 5 10

<210> SEQ ID NO 78
<211> LENGTH: 14
<212> TYPE: PRT
<213> ORGANISM: Homo Sapiens

<400> SEQUENCE: 78

Gly Pro Gly Ala Gly Ser Leu Gln Pro Leu Ala Leu Glu Gly
1 5 10

<210> SEQ ID NO 79
<211> LENGTH: 12
<212> TYPE: PRT
<213> ORGANISM: Homo Sapiens

<400> SEQUENCE: 79

```
Lys Arg Gly Ile Val Glu Gln Cys Cys Thr Ser Ile
  1               5                   10


<210> SEQ ID NO 80
<211> LENGTH: 10
<212> TYPE: PRT
<213> ORGANISM: Homo Sapiens

<400> SEQUENCE: 80

Glu Gln Lys Leu Ile Ser Glu Glu Asp Leu
  1               5                   10


<210> SEQ ID NO 81
<211> LENGTH: 75
<212> TYPE: DNA
<213> ORGANISM: Artificial
<220> FEATURE:
<223> OTHER INFORMATION: Designed using Proteomic Code (J.C.Biro)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 81
```

tgcgnganct nccnccnggn gtnagncgna cnggngtngg ntcncgagca gaagctcatc 60
tccgaggagg acctc 75

<210> SEQ ID NO 82
<211> LENGTH: 75
<212> TYPE: DNA
<213> ORGANISM: Artificial
<220> FEATURE:
<223> OTHER INFORMATION: Designed using Proteomic Code (J.C.Biro)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 82
tgccntgngt ntgnagnagn agnctngtnc cncgnacnct nggnagagca gaagctcatc 60
tccgaggagg acctc 75

<210> SEQ ID NO 83
<211> LENGTH: 75
<212> TYPE: DNA
<213> ORGANISM: Artificial

<220> FEATURE:
<223> OTHER INFORMATION: Designed using Proteomic Code (J.C.Biro)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 83
tgccncgncc ngcnccnccn gcnccnccng cnggnccnct nccncgagca gaagctcatc 60
tccgaggagg acctc 75

<210> SEQ ID NO 84
<211> LENGTH: 75
<212> TYPE: DNA
<213> ORGANISM: Artificial
<220> FEATURE:
<223> OTHER INFORMATION: Designed using Proteomic Code (J.C.Biro)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 84
tgccnccncc nggnccnagn gcngcnggnt gnctncanca nggncgagca gaagctcatc 60
tccgaggagg acctc 75

<210> SEQ ID NO 85
<211> LENGTH: 69
<212> TYPE: DNA
<213> ORGANISM: Artificial
<220> FEATURE:
<223> OTHER INFORMATION: Designed using Proteomic Code (J.C.Biro)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 85
tgcgntgntg ntanagnatn gtnccncant gncangcntg agcagaagct catctccgag 60
gaggacctc 69

<210> SEQ ID NO 86
<211> LENGTH: 30
<212> TYPE: DNA
<213> ORGANISM: Homo Sapiens

<400> SEQUENCE: 86
gagcagaagc tcatctccga ggaggacctc 30

<210> SEQ ID NO 87
<211> LENGTH: 13
<212> TYPE: PRT
<213> ORGANISM: Artificial
<220> FEATURE:
<223> OTHER INFORMATION: computer generated

<400> SEQUENCE: 87

Cys Gly Gly Glu Gln Lys Leu Ile Ser Glu Glu Asp Leu
1 5 10

<210> SEQ ID NO 88
<211> LENGTH: 26
<212> TYPE: PRT
<213> ORGANISM: Artificial
<220> FEATURE:
<223> OTHER INFORMATION: Chemically synthetized.
Designed using Proteomic Code (J.C.Biro)

<400> SEQUENCE: 88

Cys Gly Gly Ser Ser Leu Leu Val Ser Val Ala Gln Ala Ser Gly Leu
1 5 10 15

Glu Gln Lys Leu Ile Ser Glu Glu Asp Leu
20 25

<210> SEQ ID NO 89
<211> LENGTH: 26
<212> TYPE: PRT
<213> ORGANISM: Artificial
<220> FEATURE:
<223> OTHER INFORMATION: Chemically synthetized.
Designed using Proteomic Code (J.C.Biro)

<400> SEQUENCE: 89

Cys Gly Gly Glu Phe Ala Glu Gly Ala Trp Ser Leu Ala Arg Leu Val
1 5 10 15

Glu Gln Lys Leu Ile Ser Glu Glu Asp Leu
20 25

<210> SEQ ID NO 90
<211> LENGTH: 26
<212> TYPE: PRT
<213> ORGANISM: Artificial
<220> FEATURE:
<223> OTHER INFORMATION: Chemically synthetized.
Designed using Proteomic Code (J.C.Biro)

<400> SEQUENCE: 90

Cys Gly Gly Ala Pro Pro Leu Pro His Pro Arg Leu Gly Pro Ser Leu
1 5 10 15

Glu Gln Lys Leu Ile Ser Glu Glu Asp Leu
20 25

<210> SEQ ID NO 91
<211> LENGTH: 26
<212> TYPE: PRT
<213> ORGANISM: Artificial
<220> FEATURE:
<223> OTHER INFORMATION: Chemically synthetized.
Designed using Proteomic Code (J.C.Biro)

<400> SEQUENCE: 91

Cys Gly Gly Pro Gln Gly Pro Ala Pro Leu Gly Ala Cys Thr Arg Val
1 5 10 15

Glu Gln Lys Leu Ile Ser Glu Glu Asp Leu
20 25

<210> SEQ ID NO 92
<211> LENGTH: 25
<212> TYPE: PRT
<213> ORGANISM: Artificial
<220> FEATURE:
<223> OTHER INFORMATION: Chemically synthetized.
Designed using Proteomic Code (J.C.Biro)

<400> SEQUENCE: 92

Cys Gly Gly Asp Ala Asp Thr Glu Trp Cys Arg Asn Ala Met Pro Glu
1 5 10 15

Gln Lys Leu Ile Ser Glu Glu Asp Leu
20 25

SYSTEM AND METHOD TO OBTAIN OLIGO-PEPTIDES WITH SPECIFIC HIGH AFFINITY TO QUERY PROTEINS

CROSS-REFERENCE TO RELATED APPLICATION

The subject matter of the present application relates to and encompasses the disclosure of U.S. Provisional Patent Application No. 60/694,055, filed on Jun. 24, 2005 in the name of Jan Charles Biro for "A SYSTEM AND METHOD TO OBTAIN OLIGO-PEPTIDES WITH SPECIFIC HIGH AFFINITY TO QUERY PROTEINS." The disclosure of such provisional application is hereby incorporated herein by reference in its entirety, for all purposes. This application claims the benefit of U.S. Provisional Application No. 60/694,055, filed Jun. 24, 2005, under USC 119(e).

DEFINITIONS, ABBREVIATIONS

QOP: Query (or bait) Oligo-Peptide—is one short protein sequence that the target protein, designed and produced with the Method, will specifically interact.

QON: Query Oligo-Nucleotide—is a short nucleic acid sequence coding QOP.

TOP: Target Oligo-Peptide—is a short protein which is designed by the Method to specifically interact with the query protein sequence.

TON: Target Oligo-Nucleotide—is a short nucleic acid sequence coding TOP.

TOPP: Target Oligo-Peptide Pool—is a pool of different TOPs

TONP: Target Oligo-Nucleotide Pool—is a pool of TONs. TON sequences in the pool are identical regarding the corresponding $1^{st}$ and $2^{nd}$ codon residues, but may differ regarding the corresponding $2^{nd}$ codon residues.

TONT: Target Oligo-Nucleotide Template—is a single sequence where the $1^{st}$ and $3^{rd}$ codon residues are complementary to the corresponding codon residues in the QON (in reverse orientation), while the $2^{nd}$ codon residues may, but not necessarily complementary to the corresponding $2^{nd}$ codon residues in the QON.

(A Target Oligo-Nucleotide Template, which contains 15 undefined nucleic acid residues, will result in 4.sup.15=10.sup.9 different oligonucleotides (TON) which will be translated into the corresponding number of proteins, (TOP)).

BACKGROUND OF THE INVENTION

1. Field of the Invention

The present invention relates to protein-protein binding, and more particularly, to a method of determining and constructing oligo-peptides with high binding affinity for a query protein.

2. Background of the Related Art

Specific, high affinity interactions between proteins are very important in biology for processing of molecular information. The most important kinds of these specific, high-affinity protein-protein (P—P) interactions are present in: a) metabolic pathways (MP); b) regulatory pathways (RP); c) protein-receptor-protein-ligand interactions (R-L); and d) antigen-antibody (Ag-Ab) interactions.

It is necessary to understand the fundamental nature of the P—P interactions to understand and predict pathways, design artificial protein-ligands (agonists or antagonists), and/or design antibodies to known antigens. Specific High Affinity Protein Design (SHAPD) has application potential in medicine/pharmacology for the design of proteins or protein-like molecules which interact with metabolic, regulatory pathways (including stimulating or inhibiting of a protein receptor) and/or prevent or treat medical conditions which are known to be affected by antibody binding.

Current understanding of specific, high affinity protein-protein interactions are based on two main principles:

1. All information necessary to specific and unique protein folding (3D structure forming) is present in the amino acid sequence. Existing approaches are commonly classified as: (1) comparative modeling; (2) fold recognition; and (3) ab initio methods. The first two methods are knowledge based (database-driven), i.e., some template sequence, which is reliably similar to the target sequence, already exists and the sequence-structure connection is already known. True ab initio approaches rely on Anfinsen's thermodynamic principle which states that protein folding is thermodynamically determined. Thus, it is theorized that amino acid sequences contain all the necessary information to make up the correct three-dimensional structure; namely, given a proper environment, a protein would fold up spontaneously into a conformation that minimizes the total free energy of the system. However, the problem is to predict the native three-dimensional structure of a protein from its amino acid sequence.

2. The specifically interacting protein interfaces are formed by a large number of amino acids that are in a complex short-, medium-, long range cooperative interactions with each other. However, forces acting on short distances (at residue level) provide for completely different structures than forces acting on long distances and their interaction might involve many neighboring residues (cumulative effects).

Thus, none of the protein structure predicting methods perform satisfactorily, which is very frustrating because genome sequencing projects are producing numerous novel coding sequences and understanding the structure is likely required in order to understand the function. Accordingly, it would be advantageous to determine a novel method to design and produce proteins that will specifically and with high affinity interact with a query protein.

3. The theory of the Proteomic Code provided a new and fundamentally different understanding of specific and high affinity protein-protein interactions. The original concept (called the First Generation of Proteomic Code, 1981) proposed that oligopeptides coded by perfectly complementary codons will specifically and with high affinity interact with each other. However the predictability of the interacting protein design using the first generation Proteomic Code remained poor (11). Highly significant improvement was achieved by in 2006 when the Second Generation Proteomic Code has been formulated. This later concept suggests that specifically interacting proteins are coded by partially complementary codons, where the 1st and 3rd codon residues are, but the 2nd codon residue may, but not necessarily are complementary to each other, in reverse direction. The recent method is the biotechnological application of the Second Generation Proteomic Code that became known first in 2006.

SUMMARY OF THE INVENTION

In one aspect, the present invention relates to a method for designing and isolating oligo-peptides (targets) that will specifically and with high affinity interact with a known peptide (query).

In another aspect, the present invention relates to a method for determining and producing a binding amino acid sequence having binding affinity for a known amino acid sequence, the method comprising:

determining a query nucleotide sequence for the known amino acid sequence to provide a series of codons, wherein each codon has a 1.sup.st, 2.sup.nd, and 3.sup.rd nucleotide and the nucleotide sequence has a 5' and 3' end;

creating a nucleotide sequence which is complement to the query nucleotide sequence wherein the 2.sup.nd nucleotide in each codon is an undefined nucleotide;

reversing the complemented sequence;

preparing a pool of target nucleotide sequences wherein the undefined 2.sup.nd nucleotide of each codon comprises equal amounts of four relevant nucleotides and the number of nucleotide sequences in the pool is 4.sup.n wherein n is the number of amino acid residues in the known amino acid sequence;

cloning of the target nucleotide sequence pool;

preparing a target protein pool expression library from the target nucleotide sequence pool;

contacting prepared target proteins pool with known amino acid sequence; and identifying binding complexes between the known amino acid sequence and target proteins.

In yet another aspect, the present invention relates to a method for determining and producing a binding amino acid sequence (target protein) having binding affinity for a known amino acid sequence (query protein, the method comprising:

determining a query nucleotide sequence for the known amino acid sequence to provide a series of codons, wherein each codon has a 1.sup.st, 2.sup.nd, and 3.sup.rd nucleotide and the nucleotide sequence has a 5' and 3' end;

creating a nucleotide sequence which is complement to the query nucleotide sequence wherein the 2.sup.nd nucleotide in each codon is an undefined nucleotide;

reversing the complemented sequence and changing any T nucleotides to a U nucleotide;

preparing a pool of target RNA nucleotide sequences wherein the undefined 2.sup.nd nucleotide of each codon comprises equal amounts of A, U, G and C;

cloning of the target nucleotide sequence pool;

preparing a target protein pool expression library from the target nucleotide pool;

contacting prepared target proteins pool with known amino acid sequence; and identifying binding complexes between the known amino acid sequence and target proteins.

In yet another aspect, the present invention provides for a method of generating a target protein product comprising the following steps:

providing nucleic acid encoding the target protein;

transfecting a host cell with the nucleic acid or using an equivalent means for introducing the nucleic acid into the host cell; and culturing the transformed host cell under conditions suitable for expression of the target protein.

An additional aspect of the present invention relates to a diagnostic kit and method for the detection of a query protein in a test sample, comprising:

(a) incubating a test sample, which may contain a query protein with a sufficient amount of a target protein determined by the above methods, wherein the target protein is immobilized on a solid phase and incubating conditions permit the binding of the query protein to the target protein; and (b) recovering any bound query protein.

This embodiment further provides for introducing a detectable label wherein the label is capable of binding to the query protein after binding to the target protein, and determining the presence or absence of the label, to provide an indication of the presence or absence of the query protein in the test sample. The test sample may be a bodily fluid, including, but not limited to, blood, urine, semen, saliva, mucus, tears, vaginal secretions, and the like.

Other features and advantages of the invention will be apparent from the following detailed description, and claims.

BRIEF DESCRIPTION OF THE FIGURES

FIG. 1 shows the steps required to practice the method for obtaining oligo-peptides with specific high affinity to query proteins.

FIG. 2 shows representative query amino acid sequences and preparation of reverse and complement sequences wherein the second nucleotide of each codon is replaced with a variable “n” nucleotide.

Displayed sequences are sequence listed as SEQ ID NO 1, 2, 3, 4, 5, 6, 7, 8, 9.

FIG. 3 shows synthesis pattern for construction of target sequences and the progression of the permutations dependent on the number of amino acid residues.

Displayed sequences are sequence listed as SEQ ID NO 10-70.

Figure 4:
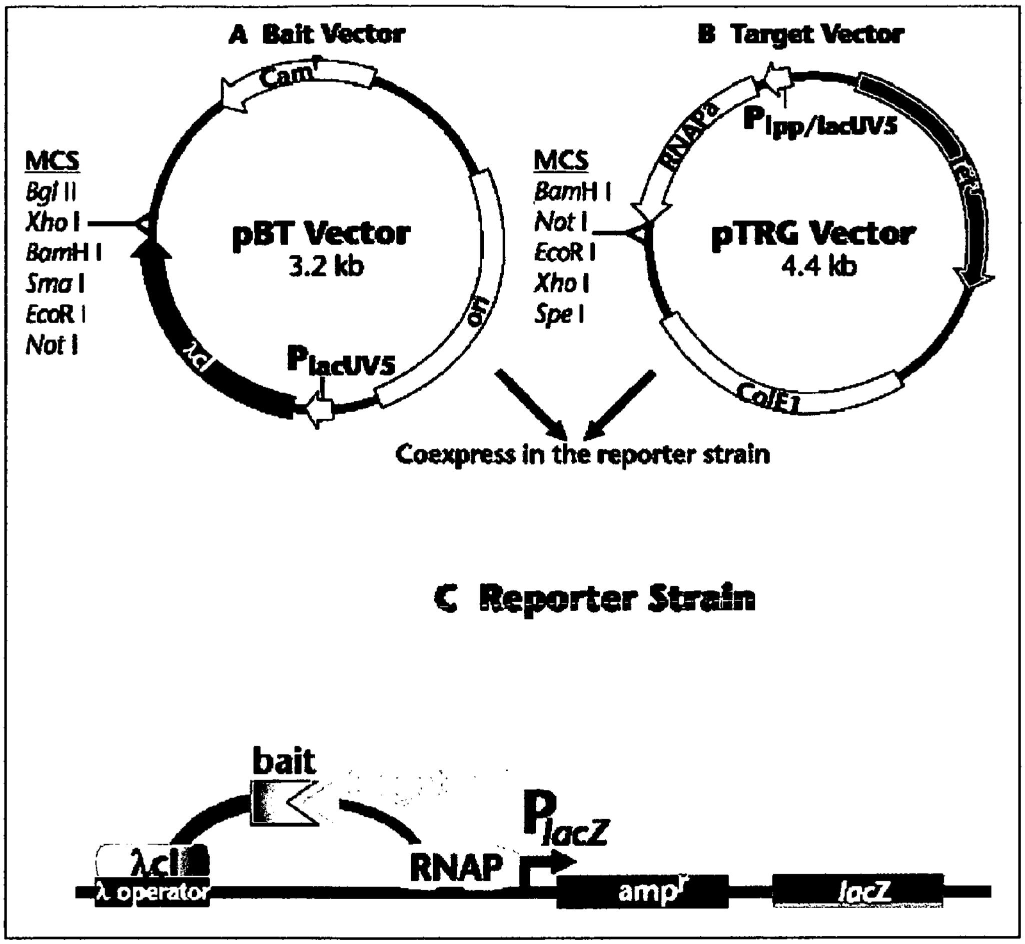

FIG. 4 shows the BacterioMatch™ Two-Hybrid System (reproduced from www.strategene.com).

FIG. 5 shows sequences, designed by the method of the invention, which were expected to produce proteins (when transcribed and translated) with the potential to specifically interact with the indicated domains of the Gal4 protein. The 1.sup.st and 3.sup.rd codon letters in these target templates are complementary to the 3.sup.rd and 1.sup.st codon letters in the Gal4 coding sequences (reverse reading direction) while the 2.sup.nd codon letter is undefined (A or T or G or C).

Displayed sequences are sequence listed as SEQ ID NO 71, 72.

FIG. 6 illustrates the transcription of TOT dsDNA will result in TOT mRNA. A 45 nucleic acid long TOT will be translated into 4.sup.15 different oligopeptides, each 15 amino acid long. Some of these oligopeptides are expected to specifically interact with the respective GAL4 targets. Displayed sequences are sequence listed as SEQ ID NO 73,74

FIG. 7. Lost of Proinsilin Query Oligo-Peptides.

Displayed sequences are sequence listed as SEQ ID NO 1, 75-80

FIG. 8. These particular designs consist of the 30-45 residue long TONTs (bold) proceeded by Cys (C) codon and followed by coding sequence of MYC tag. The sequences were ligated into cloning vectors with restrictions endonucleases. RE1 and RE2 indicate recognition sequences for these enzymes.

Displayed sequences are sequence listed as SEQ ID NO 81-86

FIG. 9. List of PINS-TOPs. These particular oligopeptides contain the PINS-TOP itself (bold) proceeded by Cys (to bound the Oligopeptide to solid surface for surface plasmon resonance (SPR) studies and Gly-Gly (spacers), and followed by MYC_COP (internal tag used as positive control).

Displayed sequences are sequence listed as SEQ ID NO 87-92.

Figure 10:
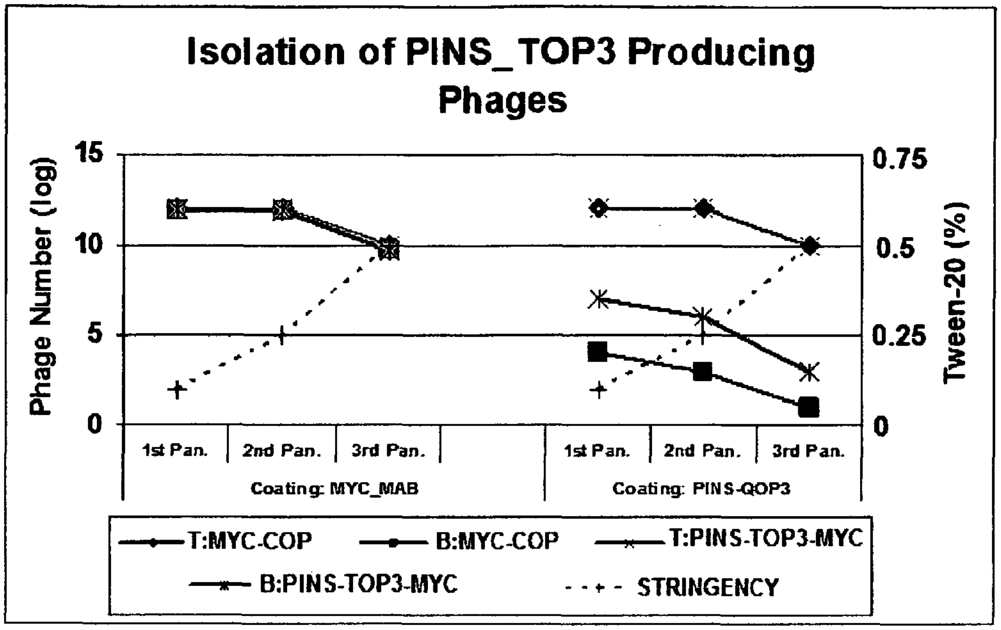

FIG. 10: Efficiency of isolation of the TOP containing phages.

The phage display library was screened for TOP producing clones by repeated pannings. In this example wells were coated with PINS3-QOP was linked and exposed to phage solution. Phages producing INS-TOP3 with strong affinity to PINS_QOP3 bound to the coated wells while the weak or no binders remained in the solution and discarded.

Wells coated with MYC antibodies (MYC_MAB) and phages producing only MYC_COP (but not any TOP) served as controls. Stringency refers to the concentration of Tween-20 (right Y) in the washing solutions used after pannings (Pan.) to remove weakly binding phages.

FIG. 11. The parameter of Query-Target bindings were determined by surface plasmon resonance (SPR) and the $K_d$ values are indicated. The binding of MYC monoclonal antibody (MAB) and bovine serum albumin (BSA) served as internal controls. N/A: non-available because $K_d$ is out of the detection limit of SPR.

DETAILED DESCRIPTION OF THE INVENTION

FIG. 1 shows the steps for producing the target proteins of the present invention having a high affinity for query proteins, wherein the primary structure is known for the query proteins. There is no limitation to the size of the query, however, preferably the sequence is from about 5 amino acid residues to about 40 amino acid residues, and more preferably from about 7 to 15 amino acid residues. Preferably, the real and natural coding sequence is known for the query protein. However, it might be some special cases when the sequence is not exactly known, for example in case of designed or artificially modified proteins. Thus, it is possible to fabricate a virtual coding sequence with back translation, using Codon Usage Frequency Tables. The present method relies on the entire information carried by the naturally occurring DNA/mRNA and not only that used for coding of the protein primary sequence.

The query sequence should be a “promising” domain of the query protein and specific domains are more important, including domains that are known to be a) antigenic; b) are located on the surface of the query protein; c) are not simple (repetitive) sequences; d) those containing less frequent amino acids; and e) those containing charged amino acid residues.

Once the promising area of the known amino acid sequence is chosen and the nucleotide sequence is determined, then construction of nucleic acid sequences encoding for the target proteins is initiated. As used herein, the term “nucleotide sequence” means a sequence of nucleotides connected by phosphodiester linkages. Nucleotide sequences are presented herein in the direction from the 5' to the 3' direction and can be a deoxyribonucleic acid (DNA) molecule or ribonucleic acid (RNA) molecule. Relevant nucleotide bases are indicated herein by a single letter code: adenine (A), guanine (G), thymine (T), cytosine (C), inosine (I) and uracil (U). The target nucleotide (RNA or DNA) prediction should follow a simple rule, namely that the 1.sup.st and 3.sup.rd codon letters of the target nucleotide sequences should be reverse-complementary to the 1.sup.st and 3.sup.rd codon nucleotide residues of the query nucleotide sequence, but the middle, 2.sup.nd residue should be any of the four possible nucleotides. The expected number of predicted target RNAs will be 4.sup.n, where n is the number of amino acids (=number of codons, =number of 2.sup.nd codon letters).

Synthesis of the nucleotide sequences can be readily prepared by, for example, directly synthesizing the fragment by chemical means, by application of nucleic acid reproduction technology, such as the PCR or by excising selected DNA fragments from recombinant plasmids containing appropriate inserts and suitable restriction enzyme sites. However, synthesis of predicted (max. 4.sup.n) sequences on a one by one basis does not seem practical. Thus, a simple mass-production is needed which will result in a mixture, containing all possible sequences in the predicted RNA/DNA pool. Fortunately, the regular nature of the nucleotides in the pool makes it possible to synthesize the entire pool of nucleotide sequences as it would be only one single nucleotide sequence. For example, the usual step-by-step (base after base) protocol can be followed except at the positions for the synthesis of the 2.sup.nd codon residue. At those points in the synthesis process, an equal mixture of the four nucleotides should be provided instead of a single nucleotide. The result of this modified oligo-nucleotide syntheses should be a mixture of the desired potential target RNAs.

Cloning the predicted and synthesized RNAs in the pool. This step is the regular cloning procedure which involves insertion of RNA into vector (plasmid or other carrier) and multiplying the sequences in bacteria or yeast as it is described in the publicly available literature. Expression vectors of the invention may comprise polynucleotides operatively linked to an enhancer-promoter, such as a prokaryotic or eukaryotic promoter. Further, an enhancer may be included in the vector. A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

Expression vectors of the present invention comprise polynucleotides that encode the target peptides of the pool. Where expression of recombinant polypeptide of the present invention is desired and a eukaryotic host is contemplated, it is most desirable to employ a vector, such as a plasmid, that incorporates a eukaryotic origin of replication. Additionally, for the purposes of expression in eukaryotic systems, one desires to position the peptide encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the different target peptides, an appropriate polyadenylation site.

The pRc/CMV vector (available from Invitrogen) is an exemplary vector for expressing a peptide in mammalian cells, particularly COS and CHO cells. Target polypeptides of the present invention under the control of a CMV promoter can be efficiently expressed in mammalian cells. The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV1-5 series of vectors, the functionally similar pCMV6b and c vectors are available from the Chiron Corp. of Emeryville, Calif. and are identical except for the orientation of the polylinker region which is reversed in one relative to the other. The pCMV vectors have been successfully expressed in simian COS cells, mouse L cells, CHO cells, and HeLa cells.

Means of transforming or transfecting cells with exogenous polynucleotide such as nucleotide molecules of the present invention are well known in the art and include techniques such as calcium-phosphate- or DEAE-dextran-mediated transfection, protoplast fusion, electroporation, liposome mediated transfection, direct microinjection and adenovirus infection.

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA or RNA within liposomes, followed by fusion of the liposomes with the cell membrane. The mechanism of how DNA or RNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest. A transfected cell can be prokaryotic or eukaryotic.

In addition to prokaryotes, eukaryotic microbes, such as yeast can also be used. *Saccharomyces* cerevisiae or common baker's yeast is the most commonly used among eukaryotic microorganisms, although a number of other strains are commonly available. For expression in *Saccharomyces*, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan. Suitable promoter sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20, VERO and HeLa cells, Chinese hamster ovary (CHO) cell lines, and W138, BHK, COSM6, COS-1, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

Following transfection, the cell is maintained under culture conditions for a period of time sufficient for expression of the target proteins of the pool. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20.degree. C. to about 50.degree. C. pH is preferably from about a value of 6.0 to a value of about 8.0, more preferably from about a value of about 6.8 to a value of about 7.8 and, most preferably about 7.4. Other biological conditions needed for transfection and expression of an encoded protein are well known in the art.

Transfected cells are maintained for a period of time sufficient for expression of the target proteins. A suitable time depends inter alia upon the cell type used and is readily determinable by a skilled artisan. Typically, maintenance time is from about 2 to about 14 days. Recovery of the target proteins comprises isolating and purifying the recombinant polypeptides. Isolation and purification techniques for polypeptides are well known in the art and include such procedures as precipitation, filtration, chromatography, electrophoresis and the like.

The target proteins are preferably arranged in a library assay system for screening with samples of the query protein. Any method which detects specific, high affinity protein-protein interactions is theoretically useful to perform the screening.

Selecting the best clones with the most specific and highest affinity interacting proteins can be followed by repeated screenings. Thus, leading to the most desired target proteins having the highest binding affinity for the query protein. The target proteins with the highest affinity are suitable for large scale target protein production.

The foregoing aspects and embodiments of the present invention are further described in the following Example. However, the present invention is not limited by the following Example, and variations will be apparent to those skilled in the art without departing from the scope of the present invention.

Example I

General Design

FIG. 2 shows the use of the present invention to obtain a Specific High Affinity Protein having binding affinity for a section of the A-peptide in the Human Insulin.

Starting with the known protein and nucleic acid sequence of the entire Pre-pro-insulin, 1-10 residues of the A peptide are selected and the corresponding nucleic acid sequence. The selected part of the peptide, called query, will be used for screening of the target protein expression library. Therefore, this sequence should be available in pure peptide form.

Next, a sequence is created which is complement to the query nucleotide sequence at 1.sup.st and 3.sup.rd codon positions but leaves the 2.sup.nd position undefined (X). The complemented sequence is reversed and in this particular example, the bases T are changed to U. The second (central) codon position remains undefined and this undefined X position can be any of possible (A, U, G, C) nucleotides. Therefore, this prediction method defines many different target RNA sequences. In the case of a sequence including 30 nucleotide bases, the expected number of possible target sequences will be .about.4.sup.10=10.sup.6.

The predicted pool of target RNAs is synthesized by following the usual step-by-step (base after base) protocol, known to those skilled in the art, except the syntheses of X positions. At the X position, a mixture of nucleotide bases are provided (which contain equal amount of A and U and G and C). The result of this modified oligo-nucleotide syntheses is a mixture of the desired potential target RNAs as shown in FIG. 3. The target RNAs are cloned and transfected, via an expression vector, into a cell for expression therein of the encoded protein. An expression library of the expressed target protein is created for screening for query protein/target protein affinity binding. When binding complexes are found to meet the affinity binding levels, the target protein may be cloned for large scale production.

These steps may be repeated numerous times by modify the length of the query sequence and/or using another domain area of the query protein that may be of interest.

Example 2

Using Bacteriomach Two Hybrid System

Example for Designing and Characterization of a Specific Protein-Protein Interaction.

The BacterioMatch™ two-hybrid system* (Stratagene, 11011 N. Torrey Pines Road La Jolla, Calif. 92037) was used to Quickly Detect Protein-Protein Interactions designed by the recent Method. It is a simple alternative or complement to yeast two-hybrid systems for in vivo detection of protein-protein interactions. Because the two-hybrid assay is performed in bacteria, results are obtained more easily and quickly than in yeast. The system is based on transcriptional activation of a primary ampicillin-resistant reporter and a secondary .beta.-galactosidase reporter for validation. The BacterioMatch two-hybrid system is based on a methodology developed by Dove, Joung, and Hochschild of Harvard Medical School.

The BacterioMatch two-hybrid system is based on transcriptional activation (FIG. 4). A protein of interest—the bait—is fused to the full-length bacteriophage repressor protein (.lamda.cI). The corresponding target protein is fused to the amino-terminal domain of the .alpha.-subunit of RNA polymerase (RNAP.alpha.). The bait is tethered to the x operator sequence upstream of the reporter promoter through the DNA-binding domain of .lamda.cI. If the bait and target interact, they recruit and stabilize the binding of RNA polymerase close to the promoter and activate the transcription of the ampicillin-resistant reporter gene in the BacterioMatch two-hybrid reporter strain. The .beta.-galactosidase reporter gene provides an additional mechanism to validate putative protein-protein interactions.

FIG. 4: The BacterioMatch™ Two-Hybrid System (Reproduced from www.strategene.com)

A. Bait Vector: The bait vector, pBT encodes the full-length bacterial phage cI protein under the control of the strong lacUV5 promoter. A protein of interest is fused to the bacterial phage .lamda.cI protein by inserting its gene into the multiple cloning site at the 3' end of the .lamda.cI gene. A multiple cloning site present makes it convenient to subclone a bait gene that is already present in many yeast two-hybrid bait plasmids.

B. Target Vector: The target plasmid, pTRG is compatible with Stratagene's cDNA library construction kit. The target plasmid directs transcription of the amino-terminal domain of RNA polymerase .alpha.-subunit and linker region under the control of tandem promoters, 1 pp and lacUV5. The target gene is fused in-frame to the .alpha.-subunit NTD through a multiple cloning site at the 3' end of the .alpha.-subunit gene.

C. Reporter Strain: The reporter strain is derived from XL1-Blue MRF'. The strain lacks all restriction systems in order to be compatible with current cDNA library construction methods. The lac I.sup.q gene located on the F' episome represses synthesis of the bait and target until induction. The reporter cassette is also located on the F' episome in the cell. The lacZ gene serves as a secondary reporter to provide a visible phenotype for identifying positive protein-protein interactions.

2. Specification (5 Biro 050825): Test of a Novel Method to Design Specifically Interacting proteins.

Target Pool is synthesized by using a Target Oligo Template (TOT) which has a Constant (C) and Variable (V) part.

The TOT-C is necessary to synthesize dsDNA of the target pool sequences and it is .about.20 nucleotides long.

The TOT-V (Target Template) is about 30-45 nucleotide long, 2/3.sup.rd of nucleotides is unambiguously defined, while 1/3.sup.rd is not (X). The X residues should be synthesized by adding a mixture of nucleotides (equal amount of A+T+G+C) to the reaction during oligo synthesis. 8. Evaluate the results (number of highly, moderately, slightly positive clones). This is done by visual inspection. 9. Save the positive clones for further experiments, which will be specified later. If there are no positive clones, it is necessary to validate the orientation and translation frame in the target mRNAs. It is possible by sequencing some target mRNAs. The sequence should show the residue pattern as under point 5.

Results

1. Both TARGET TEMPLATE to ESRLERLEQLFLLIF (GAL4 09-23AA) and TARGET TEMPLATE to QLFL- LIFPREDLDMI (GAL4 17-31AA) contained numerous positive bacterial clones growing on double selective medium.

2. Sequencing of DNA from the vectors in randomly selected positive clones confirmed that they contained the characteristic TOT pattern, i.e. defined 1.sup.st and 3.sup.rd codon residues the nucleic acids differed only in the 2.sup.nd codon positions, while they were the same regarding the 1.sup.st and 3.sup.rd codon positions.

The restrictions endonuclease recognition sequences were present,

The start and stop codons were present

The sequences were inserted into the correct, sense DNA strands

The codon frames were correct in relation to the start codon and were read in the correct frames.

3. Some positive TARGET TEMPLATE to ESRLERLEQLFLLIF (GAL4 09-23AA) clones were further processed to monoclonal colonies and proteins were extracted. Characterization of the binding properties of fluorescent labeled GAL4 peptide to the protein extract indicated the presence of saturable binding sites in the protein extracts from positive. clones and the absence of saturable binding sites in the negative clones.

The experiment below is specifically designed for using BacterioMatch (Stratagene) two-hybrid system. This system uses:

A Bait Vector (pBT) and the manufacturer's standard is an insert, the dimerisation domain of 1HBW REGULATORY PROTEIN GAL4.

A Target Vector (pTRG) and the manufacturer's standard is an insert, and .about.90 aa long mutant form of Gal11.

In the experiment below the Target Oligo Pool will be used instead of Gall 1 in the pTRG vector.

The Query in this experiment is the dimerisation domain of 1HBW REGULATORY PROTEIN GAL4 inserted into pBT (as it is provided and described by Stratagene).

The Target Oligo Templates (TOT-V) are these:

Target Oligo-Template design to specifically interact with K01486_SCGAL4_DIMDOM-171/9-23 and K01486_SCGAL4_DIMDOM-171/17/31 sequences.

Sequences below are sense, ssDNA sequences which means that the TOT-V in this sequence is the same as the sequence in the expected mRNAs (except T/U conversion).

The TOT-C is not indicated here, BPD can decide which TOT-C to use this purpose.

FIG. 5.: Sequences, designed by the Method, were expected to produce proteins (when transcribed and translated) with the potential to specifically interact with the indicated domains of the Gal4 protein. The 1.sup.st and 3.sup.rd codon letters in these target templates are complementary to the 3.sup.rd and 1.sup.st codon letters in the Gal4 coding sequences (reverse reading direction) while the 2.sup.nd codon letter is undefined (A or T or G or C).

The experiment consists of the following steps:

1. Sequence the Gal 4 DNA (provided by Stratagene) to make sure that the Query sequence is as expected.

2. Synthesize the target pool using the Target Oligo Templates

This is a single run routine oligo synthesis. Residues X are equal amount of A+T+G+C 3. Make dsDNAs This is a single run PCR 4. Make Restriction Enzyme cuts on the Target Oligo Pool sequences.

This is a single run RE reaction.

5. Insert the oligo pool sequences into the pTRG vector. about.10.sup.9 different vectors are expected Make sure that the orientation of the Target Oligo-s is correct and the transcription will result it the following mRNA. The Target Oligo Pool insertion is a single run ligase reaction. FIG. 6: Transcription of TOT dsDNA will result in TOT mRNA. A 45 nucleic acid long TOT will be translated into 4.sup.15 different oligopeptides, each 15 amino acid long. Some of these oligopeptides are expected to specifically interact with the respective GAL4 targets. 6. Insert the vectors into bacteria. 7. Perform the BacterioMatch two-hybrid assay accordingly to the Stratagene manual.

K.sub.d of the binding sites varied between (Kd~100 nM-100 μM range) indicating the presence of limited number of high affinity binding sites. 4. Unlabelled GAL4 inhibited the binding of labeled GAL4 to the proteins from positive clones while other randomly chosen proteins (insulin, growth hormone, prolactin) were ineffective competitors even in much higher concentrations.

This experiments indicate that it is possible to design specifically interacting oligo-peptides (target) to any oligo-peptide (query) and detect the interaction in bacterial 2 hybrid system (like BacterioMatch™). This method is quick, it takes only some days to obtain specifically and with high affinity interacting monoclonal proteins. The designed protein-protein interaction is highly specific and has high affinity. Kd~100 nM-100 μM range

Example 3

Using Phage Display

A routine phage display method [9] was used for identifying and producing short high affinity & specifically interacting oligopeptides to 5 distinguished domains of human prepro-657 insulin peptide (FIG. 7, SEQ ID NO 1, 75-80). Five target oligonucleotide templates (TONT) were designed using the native CDS of the query oligopeptides (QOP). The templates (a variable nucleic acid sequence where the $1^{St}$ and $3^{rd}$ codon residues are defined while the $2^{nd}$ codon residue remains undefined) were completed with non-variable codons/residues to add leader sequence, recognition sites for restrictions endonuclease, start/stop codons and coding sequence for MYC protein (MYC-CON). (MYC is a well known protein with commercially available antibodies and it is widely used as positive control to monitor different cloning procedures). (FIG. 8, SEQ ID NO 81-86).

Care was taken to monitor the TONT-MYC sequences for potential binding sites for restrictions enzymes as well as for potential stop codons, because these sequences could truncate some of the nucleic acids in the Target Oligonucleotide Pools (TONP). The risk for truncation by restrictions enzymes was seduced when the enzyme had long (5-6 residues) recognition site.

Pools of target oligo-nucleotides (TONP) were synthesized by manual method where an equal mixture of dATP/dCTP/dGTP/dTTP were provided at every N positions (central codon residue). By this way the number of different nucleotides in the pool became, say $\sim 4^{10} = \sim 10^6$ (derived from a 10 codons long TONT). The oligonucleotide pools were purified on 8% non-denaturing PAGE, followed by treatment with T4 kinase to obtain dsDNAs. The sequences were treated with Acc651 (G'GTACC) and NotI (GC'GGCCGC) and inserted into M13KE vector (into the correct site and correct orientation) and electro-porated. The expressions libraries were titrated and the quality of some individual DNA sequences in the TON-MYC pools were checked by resequencing. The phages were propagating in ER2738 (*E. coli*) cells (see laboratory manuals for details of these routine laboratory procedures).

The phage display libraries were enriched by repeated pannings for particular colonies which were producing the requested affinity proteins. The 5 query oligopeptides (QOP) were chemically synthesized and bound to the surface of dishes. The affinity protein producing phages bound to these coated surfaces, while other phages were easily removed by repeated washing. The surface-bound phages were further multiplied and submitted to the subsequent, similar panning procedure. The efficiency of cloning, protein expression and pannings were monitored (FIG. 10).

The selectivity and efficiency of pannings (stringency) was successfully increased by increasing the concentration of Twin-20 in the washing solution from 0.1 to 0.5%

After the $3^{rd}$ panning the plates were repeatedly washed with TBST (TBS+0.5% tween-20) which left only about $10^3$ phages bound (the strongest binders to the QOPs out of $\sim 2\times10^{10}$ input phages). These strongest binders were amplified and 100 well isolated plaques were randomly selected for final amplification, DNA extraction and sequencing. The DNA sequences corresponding to the TONs were translated (using the universal genetic code, Table I) and the oligopeptides were chemically synthesized.

The binding kinetics between QOPs and TOPs were determined by Surface Plasmon Resonance (SPR, BIACORE). The TOPs (FIG. 9). were immobilized on the chips using thiol-disulphate exchange method It showed specific (selective) binding of TOPs to their corresponding QOPs and these bindings had high affinity. (FIG. 11).

Discussion

1., Proteomic Code is not a hypotheses, this is a 30 years old concept first proposed by me in 1981 and it's original suggestion (perfect complementary coding of collocating amino acids) was tested by many and many well working examples were found [or review see ref 6]. The recent invention is based on the partial complementarity coding of co-locating amino acids,—this is the novelty in the invention.

2., Regarding the theoretical background of the invention a., The original hypotheses of the Proteomic Code (from 1981) suggested the perfect reverse complementarity of the codons behind co-locating amino acids, like the 5-ATG-3'/3'-TAC-5' formula. You can find hundreds of well working examples for this from different laboratories [7,8].

b., However there were unexpected exceptions. Therefore I revised the original hypotheses and suggested the second generation of Proteomic Codes, where the $1^{St}$ and $3^{rd}$ codon residues are defined, while the second codon residues remain undefined behind the co-locating amino acids, like 5'ANG-3'/3'-TNC-5' formula.

c., By this way the original 5-ATG-3'/3'-TAC-5'-like formula became the subdivision of the recently used 5'ANG-3'/3'-TNC-5'-like formula. This later Proteomic Code permits 1:4 uncertainty (per codon) of the predictions. However please note that this is a much better prediction than the 1:20 uncertainty (per amino acid) provided by the random oligopeptide syntheses. It means that if you want to find, say, interacting decapeptides using random method you have to screen a peptide library containing $20^{10}$ different sequences. Using the 5'ANG-3'/3'-TNC-5' type formula you can reduce this number to $4^{10}$, which is $10^{13}/10^6$ improvement. This is the novelty and industrial application of the recent patent suggestion.

d., We found, that Nature uses the 5'ANG-3'/3'-TNC-5' type proteomic code to define collocating amino acids. This was found by using a bioinformatical tool, called SeqX. The tool picks up co-locating amino acids which are not defined by the suggested Proteomic Code. Fortunately it is not cases any methodological problems. The specific and non-specific hits are possible to separate of each other: the number of nonspecific hits corresponds to the number of random hits, while the number of specific hits are significantly higher than the number of calculated random hits. This is thoroughly discussed in most of our publication, especially in [10].

e., We are very clear, that the recent invention is to produce specifically and with high affinity interacting oligo-peptides. This method was inspired by bioinformatical studies performed on individual peptides. It is known, that short residue-to-residue-type interactions are very frequent within protein molecules (like parallel alpha helices and beta sheets) and they provide a stable 3D structure to the peptides. It is reasonable to believe, that interactions between large peptides (like antigen-antibody, receptor-ligand) are more complex than the relatively simple oligopeptide interactions within the protein structures. The recent invention doesn't require the full understanding of macromolecular interactions. Therefore we prefer not to involve any of our observations or experiment concerning the application of Proteomic Code for interactions between large peptides.

f., the controversial statement that the unit of specific protein-protein interactions are the amino acid themselves is not at all controversial if you have a look at the parallel alpha helices and beta shifts. They are far away from the familiar "docking-type" of interactions.

g., the controversial statement that the nucleic acids contain additional information to the genetic code is not at all controversial if you consider that The information density of nucleic acids is $\log_2 64=6$ bits/codon The information density of proteins is $\log_2 20=4.3$ bites/residue.

The Genetic Code doesn't explain the difference.

Predictability of the Results

It is to emphasize, that the Proteomic Code applied in this method is not a mathematical formula which gives exactly predictable result regarding the sequence of one specifically interacting oligopeptide (TOP). (If it were this wouldn't be patentable). The proteomic code itself provide a large number of sequences (TOPs) with the potential for specific interaction with the query protein (QOP). The second codon residues are undefined in the TONTs giving a degree of randomness and uncertainty into the outcome of the process. However this randomness is limited, the number sequences in the TONPs is much smaller than the number of sequences provided by perfectly random selection of the 20 amino acids into a sequence.

Another inherent uncertainty of the method, that screening of an expression library with the QOP will provide more than one interacting proteins (strong TOP binders). In the example 3 we obtained ~1.000 strongly binding phages after the $3^{rd}$ panning. We sequenced only ~100, each slightly different from each other. It is no way to predict which sequence represent the strongest and most specific binding oligopeptides. Only synthesizing a large number of pre-selected proteins and measuring the affinity parameters will give the correct answer. However this slight sequence diversity of TOPs provides possibility to involve additional criteria to select the "best" TOPs for industrial applications (like chemical stability, toxicity, et cetera).

Rare nucleotides such as inosine present in the nucleic acids should be treated as their structurally and functionally closest relative between frequent (canonical) nucleotides.

Unexpected Results

"The recent Method—based on the rules of the 'second generation Proteomic Code'—is far superior and much more reliable to identify specifically and with high affinity interacting oligopeptides than the simple method known in the prior art that uses the simple rule of the 'first generation Proteomic Code'.

We have used so far as much as 21 different query oligopeptides and was able to identify and characterize as much as different target oligopeptides (average 18 TOP/QOP) each having high affinity and specific binding to its own QOP (Kd<100/uM). Only two of the TOPs (0.5%) were coded by CDS containing >70% perfectly complementary codons to the codons in CDS of their corresponding QOPs."

INDUSTRIAL APPLICATIONS

The present invention thus relates to a unique in silico method of identifying the most effective binding proteins to interact with reactive epitopes on a respective protein antigen. Epitopes of a protein antigen represent the sites that are recognized as binding sites by certain immunoglobulin molecules, as antibodies.

The benefits of the present invention are widespread and beneficial to biotechnology, and are useful, for example, in developing drugs for treatment of viral diseases such as AIDS and influenza, as well as diseases such as Alzheimer's and Mad Cow (bovine spongiform encephalopathy) diseases In addition to medical research and drug development, the present invention has applications related to environmental health and public safety, including for example the detection of bacteria, viruses, toxins, etc. in air, water, and food supplies.

By way of further specific examples, the present invention has applications in the following areas:

1. improving health-care, by providing a new and easily implement an approach to development of diagnostic kits and therapeutic drugs;
2. improving the environment, by providing new and economic approaches to detecting environmental pathogens;
3. improving working conditions of workers, by providing economic and effective ways to detect environmental pathogens; and
4. improving homeland security, by providing rapid detection of known as well as new pathogens in air, water, food, etc.

SEQUENCE LISTING 1-92 attached on CD and separate text file

That which is claimed is:

1. A method for determining and producing a binding amino acid sequence (target oligopeptide) having binding affinity for a known amino acid sequence (query protein), the method comprising:

a) determining a query nucleotide sequence which encodes the query oligopeptide to provide a series of codons, wherein each codon has a $1^{st}$, $2^{nd}$, and $3^{rd}$ nucleotide and the nucleotide sequence has a 5' and 3' end;

b) creating a nucleotide sequence which is complementary to the query nucleotide sequence, except that the $2^{nd}$ nucleotide in each codon is an undefined nucleotide;

c) determining the reverse sequence of the created nucleotide sequence;

d) preparing a pool of target nucleotide sequences wherein the undefined $2^{nd}$ nucleotide of each codon comprises equal amounts of A, T/U,G,C nucleotides;

e) cloning the target nucleotide sequence pool;

f) preparing a protein expression library from the target nucleotide sequence pool;

g) contacting the prepared expression library with the query protein; and h) identifying binding complexes between the query protein and one or more target oligopeptides.

2. The method of claim 1, further comprising:

providing a nucleic acid encoding a target oligopeptide identified in step h);

introducing the nucleic acid into a host cell to create a transformed host cell; and culturing the transformed host cell under conditions suitable for expression of the target oligopeptide.

* * * * *